United States Patent
Krupa

(10) Patent No.: US 9,266,795 B2
(45) Date of Patent: Feb. 23, 2016

(54) PROCESS FOR THE PURIFICATION OF 1,3-BUTADIENE FROM AN OXIDATIVE DEHYDROGENATION PROCESS

(71) Applicant: UOP LLC, Des Plaines, IL (US)

(72) Inventor: Steven L. Krupa, Fox River Grove, IL (US)

(73) Assignee: UOP LLC, Des Plaines, IL (US)

( * ) Notice: Subject to any disclaimer, the term of this patent is extended or adjusted under 35 U.S.C. 154(b) by 541 days.

(21) Appl. No.: 13/852,534

(22) Filed: Mar. 28, 2013

(65) Prior Publication Data

US 2014/0296589 A1  Oct. 2, 2014

(51) Int. Cl.
*C07C 5/327* (2006.01)
*C07C 7/00* (2006.01)
*C07C 7/08* (2006.01)

(52) U.S. Cl.
CPC .. *C07C 7/005* (2013.01); *C07C 7/08* (2013.01)

(58) Field of Classification Search
USPC ........ 203/14, 45, 46, 43, 44, 42, 60, 2, 50, 98
See application file for complete search history.

(56) References Cited

U.S. PATENT DOCUMENTS

| | | | |
|---|---|---|---|
| 2,963,522 A | 12/1960 | Cobb | |
| 3,232,850 A | 2/1966 | Graham | |
| 4,128,457 A * | 12/1978 | Barba | C07C 7/08 203/29 |
| 4,504,692 A * | 3/1985 | Arakawa | C07C 11/167 585/616 |
| 5,003,112 A | 3/1991 | Knifton | |
| 6,156,947 A | 12/2000 | Vora | |
| 7,030,284 B2 | 4/2006 | Shutt | |
| 7,227,047 B2 | 6/2007 | Risch | |
| 7,566,799 B2 | 7/2009 | Steinbrenner | |
| 2008/0119675 A1* | 5/2008 | Coupard | B01D 3/14 585/264 |
| 2008/0183024 A1* | 7/2008 | Klanner | C07C 5/3337 585/633 |
| 2012/0041244 A1 | 2/2012 | Montalbano | |
| 2012/0253059 A1 | 10/2012 | Caers | |

OTHER PUBLICATIONS

PCT International Search Report for PCT/US2014/031812, mailed Jul. 29, 2014.
U.S. Appl. No. 13/852,473, Bozzano, filed Mar. 28, 2013.
U.S. Appl. No. 13/852,047, Bozzano, filed Mar. 28, 2013.

* cited by examiner

*Primary Examiner* — In Suk Bullock
*Assistant Examiner* — Sharon Pregler

(57) ABSTRACT

A process is presented for the purification of 1,3 butadiene. The process is for treating a butadiene stream from an oxidative dehydrogenation unit, where a butane stream is dehydrogenated, generating a butadiene rich stream. The butadiene rich stream is fractionated and passed through a butadiene recovery unit. Additional C4 compounds recovered from the fractionation bottoms stream are further processed for increasing yields of butadiene.

15 Claims, 1 Drawing Sheet

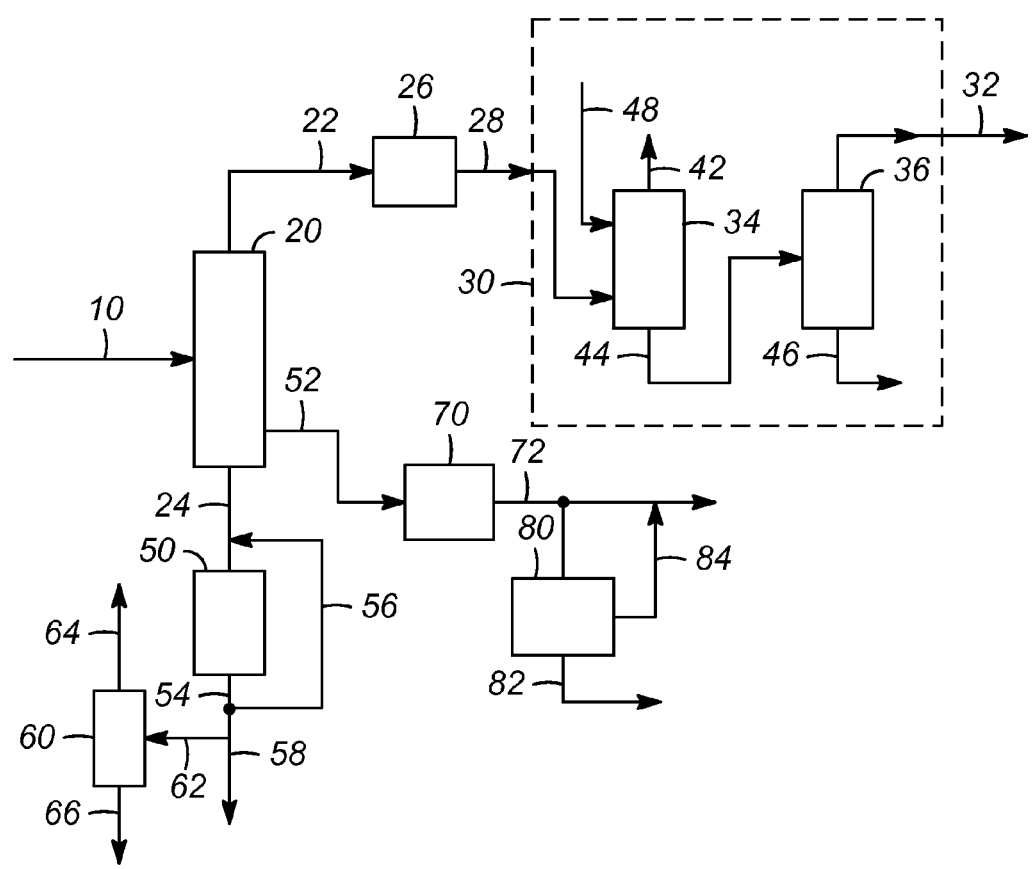

PROCESS FOR THE PURIFICATION OF 1,3-BUTADIENE FROM AN OXIDATIVE DEHYDROGENATION PROCESS

FIELD OF THE INVENTION

The field of the invention relates to the dehydrogenation of hydrocarbons. Specifically, the invention relates to the dehydrogenation of light hydrocarbons using an oxidative dehydrogenation process.

BACKGROUND OF THE INVENTION

Butadiene is an important monomer for the production of high molecular weight polymers. It is used extensively in the production of tires and other products in the automotive industry. It is also used extensively in the production of synthetic rubbers, such as styrene-butadiene rubber, nitrile-butadiene rubber, and styrene-butadiene latex. Polymer grade butadiene requires a high purity, and needs to be essentially free of active chemicals such as acetylenes, carbonyls, and contaminants such as sulfur and other heavy components.

Butadiene is usually a by-product recovered from the steam cracking of naphtha during the production of ethylene and propylene. Naphtha cracking, either through steam or catalytic cracking, produces a range of products, and is not optimized for the production of chemicals such as butadiene. Another route for the production of butadiene is through catalytic oxidative dehydrogenation of n-butene, which yields a higher concentration of butadiene, but also yields some undesirable products that must be removed.

SUMMARY OF THE INVENTION

The present invention is for the production of a purified stream of 1,3 butadiene, where the butadiene is generated from an oxidative dehydrogenation process. The oxidative dehydrogenation of a butene stream generates a crude butadiene stream. While the process generates relatively high levels of oxygenates, including aldehydes and furan, the process does not generate isobutylene or isobutane, thereby simplifying the separation and purification process.

The process includes passing the crude butadiene stream to a butadiene fractionation unit generating an overhead stream comprising 1,3-butadiene and 1-butene, and a bottoms stream comprising oxygenates, other C4 compounds and heavier hydrocarbons. The overhead stream is passed to a butadiene recovery unit for generating a purified butadiene stream and a second stream comprising 1-butene.

The bottoms stream generated from the butadiene fractionation unit can be further processed to increase butadiene yields. The first step in processing the bottoms stream is to separate C4 hydrocarbons and recycle the C4 hydrocarbons back to the dehydrogenation unit. The C4 hydrocarbon stream can also be separated and processed to pass butenes to a dimerization unit for generating octenes. The octenes can be further processed to generate p-xylene.

In another embodiment, the bottoms stream includes vinyl acetylene. The vinyl acetylene can be passed to a selective hydrogenation unit to convert vinyl acetylene to n-butenes. The resulting process stream from the selective hydrogenation unit is then passed to the butadiene fraction unit to recover the additional butene-1 and butene-2 produced for further processing.

Other objects, advantages and applications of the present invention will become apparent to those skilled in the art from the following detailed description and drawings.

BRIEF DESCRIPTION OF THE DRAWING

The FIGURE is a process for the production of polymer grade 1,3-butadiene.

DETAILED DESCRIPTION OF THE INVENTION

The production of butadiene can be performed with oxidative dehydrogenation of n-butene. The oxidative dehydrogenation process provides an attractive route for the production of butadiene as there are lower concentrations of undesirable compounds that need to be removed, such as isobutylene or isobutane. This reduces separation costs due to fewer similar boiling point compounds.

Oxidative dehydrogenation is a process of dehydrogenation of n-butenes through contacting the paraffin with a catalyst. Oxidative dehydrogenation is an exothermic process that avoids some of the thermodynamic constraints of non-oxidative dehydrogenation processes by forming water as a by-product. In addition, carbon deposition is minimized, or eliminated, for a more stable catalytic process.

Oxidative dehydrogenation utilizes a catalyst such as vanadium oxide, molybdenum oxide, chromium oxide, or a vanadium-magnesium oxide catalyst, or even a combination of the metal oxides on a support. Supports can include aluminas, zirconia, titania, magnesia, and other refractory materials.

Oxidative dehydrogenation of butenes generates a crude butadiene stream which has a relatively high concentration of 1,3 butadiene, but also includes higher levels of oxygenates, such as aldehydes, over a typical process stream from a steam cracker crude C4 stream. In addition to the high levels of aldehydes, a major contaminant is furan, and can be as high as 2500 ppm by weight. The furan will not be removed with a sodium bisulfate wash, but will require additional processing by solvent extraction or fractionation. The oxygenates need to be removed to avoid negative impacts on downstream processing units. The use of oxidative dehydrogenation for the production of butadiene generates a crude product stream that lacks isobutylene, isobutane or C3 and lighter hydrocarbons in the starting feed. This allows for fractionation of the feed through a single fractionation unit and without the use of a selective hydrogenation process, such as UOP's KLP™ process. Thus providing a savings in energy and equipment.

The present invention comprises a process, as shown in the FIGURE, for purifying a crude butadiene stream. The process includes passing a crude butadiene stream 10 to a butene-2 column 20. The butene-2 column generates an overhead stream 22 comprising 1,3 butadiene, and a bottoms stream 24 comprising oxygenates and heavier components. The overhead stream 22 is passed to a butadiene extraction unit 30 to generate a purified 1,3-butadiene product stream 32. The process can, optionally, include a wash to remove residual oxygenates in the overhead stream 22, where the overhead stream 22 is passed to a wash 26, to generate a washed butadiene stream 28. The washed stream 28 is then passed to the butadiene extraction unit 30.

The butene-2 column 20 is a super-fractionator, and is designed in a single shell. A super-fractionator is a system where there is separation of a multicomponent mixture, and in this case, the overhead condenser serves as a super-fractionation stage, and the overhead stream is partially condensed with the product stream remaining in the vapor phase. Super-fractionators are used to separate streams with close relative volatilities between key components, and have high internal vapor and liquid flow rates. This generates a purified overhead stream with the bottoms stream comprising the bulk of the remaining components.

The butene-2 column utilizes UOP's MD tray applications for maximum distillation efficiency. The MD trays are multiple downcomer trays for providing high liquid and vapor throughput in a distillation column. The MD trays can include slotted sieve trays, trays having long weir length and large downcomer areas to provide for high liquid handling capabilities.

The butadiene extraction unit 30 comprises an extractive distillation column 34 and a solvent recovery, also known as a solvent rectifier, column 36. The extraction unit 30 for producing a purified butadiene product comprises passing the butadiene stream 22 to the extractive distillation column 34 to generate an overhead stream 42 comprising 1-butene, and a bottoms stream 44 comprising butadiene and an extractive solvent. The bottoms stream 44 is passed to the solvent recovery distillation column 36 to generate an overhead stream 32 comprising the purified 1,3-butadiene, and a bottoms stream 46 comprising the extraction solvent. The extraction solvent is recycled to the extractive distillation column 34 as an inlet stream 48. Extractive solvents used in the extractive distillation of butadiene can include N-methylpyrrolidone (NMP), dimethylformamide (DMF), dimethyl acetamide, and acetonitrile. A common extractive solvent is NMP.

The process is further designed to increase the butadiene yields by conversion of by-products in the crude butadiene stream. The butene-2 column 20 generates a bottoms stream 24 which comprises other C4 hydrocarbon compounds. The bottoms stream 24 can be passed to a second column (not shown) to generate an overhead stream comprising n-butane and 2-butene, and a bottoms stream comprising vinyl acetylene and oxygenates. One aspect is the issue of separating acetylenes. When there are acetylene rich streams, there is some internal recycle of product, possibly including 2-butenes, into the acetylene rich streams to maintain the acetylene concentration below the explosive limit. The butene-2 column 20 will be designed and operated to ensure a dilution of the acetylene stream to a safe concentration limit, as is known to one skilled in the art of 1,3 butadiene processing.

In an alternative, a side-draw stream 52 is withdrawn from the butene-2 column to generate a side-draw stream 52 comprising n-butane and 2-butene. The bottoms stream 24 comprising vinyl acetylene is passed to a selective hydrogenation process unit 50 to generate a process stream 54 comprising butenes. The process stream 54 is subsequently processed based upon the content of the process stream and the content of the feeds stream 24. A first portion of the process stream 62 is passed to a separation column 60 to generate an overhead stream 64 comprising butenes, and a bottoms stream 66 comprising oxygenates and heavier hydrocarbons. The overhead stream 64 can be passed to the butene-2 column 20 for recovery of the butene-1 and butene-2 for further processing. An advantage for passing the overhead stream 64 to the butene-2 column is that it gives the plant operator control over where to maximize net yield by how the selective hydrogenation zone is designed. In addition to the hydrogenation of VA to 1-butene and 2-butene, isomerization of 1-butene to 2-butene can be performed, thus allowing for control of either 1-butene product, or 1,3-butadiene product through further processing of the 2-butene. This allows for shifting of the product streams based upon economics, or production needs. In an alternative, the overhead stream 64 can be passed directly to a dehydrogenation unit for conversion of all 1-butene and 2-butene to 1,3-butadiene.

In an alternative, the vinyl acetylene dilution can be accomplished through allowing a portion of the heavies in the separation column 60 to leave in the overhead stream 64. The heavies, comprising C5 and C6 hydrocarbons, then recycle to a higher concentration in the butene-2 column, and therefore in the bottoms stream 24. In this manner, the VA is diluted with C5/C6 and reduces the amount of C4s dragged into the bottoms stream 24 for VA dilution. This allows for increased C4 recovery for passing to dehydrogenation.

A second portion of the process stream 56 can be recycled to the selective hydrogenation unit as a diluent to help control the exotherm in the selective hydrogenation reactor. A third portion of the process stream can be used as a purge to control the build up of oxygenates and heavier components. The purge stream 58 can be passed to downstream process units when the separation column 60 is not present for the removal of heavies.

In an alternative to separating the bottoms stream 24, C4s can be recovered through a side draw. The side draw stream 52 comprising butenes can be passed to the oxidative dehydrogenation reactor to convert the recovered butenes to 1,3-butadiene. The side draw includes separating out C4 and returning heavies to the butene-2 column. Processing the side draw stream 52 can also include passing the side-draw stream through a wash unit 70 to generate a butene rich stream 72 with reduced oxygenate content. The wash unit 70 removes aldehydes and other oxygenates generated in the oxidative dehydrogenation process. The washed stream 72 can be passed to a dimerization unit 80 to generate a process stream 82 comprising C8 compounds, including octenes, and a raffinate stream 84 comprising C4 compounds.

The process can further include passing the C8 compounds stream 82 to a reformer. The reformer can process the octenes to generate xylenes, and in particular p-xylenes. P-xylenes are useful precursors for a variety of compounds, including polymers. The raffinate stream 84 from the dimerization unit 80 can be passed back to the dehydrogenation unit. The butadienes generated by the dehydrogenation unit can be passed to the butene-2 column for recovery of the additional 1,3-butadiene.

As an alternate, the side-draw stream 52, comprising C4 compounds, can be either washed and passed to the dehydrogenation unit, or directly passed to the dehydrogenation unit, and subsequently passed to the butene-2 column to increase the 1,3-butadiene yield.

The crude process stream 10 comprising butadiene is full of reactive chemical components. The control and prevention of reactions can include adding an anti-oxidizing agent, or an anti-polymerizing agent to the crude process stream 10.

EXAMPLE

A crude butadiene stream was generated by an oxidative dehydrogenation process. The crude stream composition is shown in Table 1 as mass %, and the feed rate was approximately 15,000 kg/hr. The butene-2 column generated an overhead stream comprising 1,3 butadiene and 1-n-butene.

TABLE 1

Butene-2 column separation of crude butadiene process stream

| compound | feed | overhead | bottoms | Sidedraw | bottoms |
|---|---|---|---|---|---|
| n1C4= | 3.8 | 4.8 | | | |
| 1,3 BD | 75.3 | 95.2 | | | |
| NC4 | 2.7 | | 12.8 | 13.5 | |
| t-2C4= | 11.1 | | 53.3 | 55.9 | |
| c-2C4= | 6.1 | | 29.2 | 30.6 | |
| VA | .4 | | 2 | | 42.8 |
| Oxygenates | 0.6 | | 2.7 | | 57.2 |

TABLE 1-continued

Butene-2 column separation of crude butadiene process stream

| compound | feed | overhead | bottoms | Sidedraw | bottoms |
|---|---|---|---|---|---|
| and heavies | | | | | |

The example shows the single stage separation of butadiene and 1-butene from the other components. The table also shows two alternatives: the composition of the bottoms stream taken as a single bottoms stream, or the alternative sidedraw stream with the remaining bottoms stream comprising oxygenates and heavies. This example also shows an idealized separation for illustrative purposes, such as no C4's in the bottoms stream. The actual bottoms stream will include sufficient other hydrocarbons, including C4's, for the safe dilution of the vinyl acetylene (VA).

The relatively small amount of vinyl acetylene (VA) indicates an advantage for using a small selective hydrogenation process (SHP) unit for the conversion of VA to n-butenes, thus reducing the size of the stream requiring selective hydrogenation, as well as reducing the amount of SHP catalysts. The SHP catalysts are also less sensitive to oxygenates and sulfur over the catalysts used in the usual commercial KLP process. The VA converted to n-butenese can be passed to the butene-2 column for further processing.

The 1-butene recovered from the butadiene extraction unit is also polymer grade, high value co-product. The sidedraw process stream can be directly recycled to the oxidative dehydrogenation unit, or further processed to make other net products.

Both the butene-2 column overhead stream and the sidedraw stream can be washed with a sodium bisulfate wash to remove any residual carbonyl compounds that are in the overhead stream or the side-draw stream. The wash is added when the residual oxygenates are problematic for downstream process units, or for product quality.

The butene-2 column bottoms contains mostly 2-butent and n-butane. This can be recycled directly to the dehydrogenation unit. The bottoms stream can also be separated and processed with smaller units. The oxygenates in the bottoms stream comprise a relatively large amount of furan. The high furan control can also be beneficial in that furan competes with the olefins for adsorbed sites on the catalyst. While not being held to any particular theory, it is believed, this can reduce butene hydrogenation and hydrogen consumption to maximize 1-butene selectivity.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for the purification of 1,3-butadiene, comprising:
  passing a butadiene stream to a butene-2 column, thereby generating an overhead stream comprising butadiene, a side draw stream comprising n-butane and 2-butene, and a bottoms stream comprising vinyl acetylene, oxygenates, and heavier hydrocarbons;
  passing the overhead stream to a butadiene extraction unit, thereby generating a purified 1,3-butadiene product stream;
  passing the side draw stream to a dimerization unit to generate a process stream comprising octene and a raffinate stream;
  passing the raffinate stream to a dehydrogenation unit to generate a dehydrogenation process stream comprising butadiene;
  passing a portion of the bottoms stream to a selective hydrogenation process to generate a selective hydrogenation process stream comprising n-butane, 2-butene, and butadiene;
  passing the dehydrogenation process stream and the hydrogenation process stream to the butene-2 column.

2. The process of claim 1 wherein the butadiene extraction unit comprises:
  passing the overhead stream to an extractive distillation column to generate an overhead stream comprising 1-butene, and a bottoms stream comprising butadiene and an extractive solvent; and
  passing the bottoms stream to a solvent recovery distillation column to generate an overhead stream comprising purified butadiene and a bottoms stream comprising the extraction solvent.

3. The process of claim 1 further comprising passing the bottoms stream to a second column to generate a second overhead stream comprising n-butane and 2-butene, and a second bottoms stream comprising vinyl acetylene.

4. The process of claim 1 wherein the butene-2 column includes passing the butene-2 bottoms to a second column, and wherein the second column generates a second column overhead stream comprising n-butane and 2-butene, with bottoms stream comprising heavies.

5. The process of claim 2 wherein the extraction solvent is selected from the group consisting of N-methylpyrrolidone (NMP), dimethylformamide (DMF), dimethyl acetamide, and acetonitrile.

6. The process of claim 1 further comprising passing the side draw stream to a wash to generate a washed stream comprising n-butane and 2-butene.

7. The process of claim 1 further comprising passing the octene process stream to a reformer to generate a process stream comprising p-xylene.

8. The process of claim 1 further comprising passing the selective hydrogenation process stream to a C4 column to generate an overhead stream comprising the 2-butenes, and a bottoms stream comprising heavier hydrocarbons and oxygenates.

9. The process of claim 8 further comprising passing the C4 overhead stream to the butene-2 column.

10. The process of claim 1 further comprising the injection of an anti-oxidant, or an anti-polymerant into the feedstream to the butene-2 column.

11. The process of claim 1 further comprising:
  passing the overhead stream to a wash prior to passing the overhead stream to the butadiene extraction unit, thereby generating a washed butadiene stream, wherein the wash comprises contacting the butadiene overhead stream with a sodium bisulfite solution;
  passing the washed butadiene stream to the butadiene extraction unit, thereby generated a purified butadiene product stream.

12. A process for the production of 1,3-butadiene, comprising:
  passing a butene stream to an oxidative dehydrogenation unit to generate an oxidative dehydrogenation process stream comprising butadiene;
  passing the butadiene to a butadiene separation unit to generate a first stream comprising butadiene, a second stream comprising n-butane and 2-butene, and a third stream comprising vinyl acetylene, oxygenates and C5/C6 hydrocarbons;

passing the first stream to a wash to generate a washed first stream;

passing the washed first stream to a butadiene extraction unit to generate a purified butadiene stream;

passing the second stream to a dehydrogenation unit to generate a fourth stream comprising butadiene;

passing the fourth stream to the butadiene separation unit;

passing the third stream to a selective hydrogenation unit to generate a selective hydrogenation process stream comprising butenes;

passing the selective hydrogenation process stream to a second separation unit to generate a fifth stream comprising n-butenes, and a sixth stream comprising oxygenates and C5+ hydrocarbons; and passing the fifth stream to the butadiene separation unit.

13. The process of claim 12 wherein the butadiene extraction unit comprises an extractive distillation system.

14. The process of claim 12 further comprising passing the second stream to a dimerization unit to generate a dimerization process stream comprising octenes.

15. The process of claim 14 further comprising passing the octenes to a reforming unit to generate a process stream comprising p-xylenes.

* * * * *